US00PP37738P2

(12) United States Plant Patent
Chen et al.

(10) Patent No.: US PP37,738 P2
(45) Date of Patent: Oct. 6, 2026

(54) PEACH TREE NAMED 'USDA-ARS Summer Joy'

(50) Latin Name: ***Prunus persica* [*L.*] *Batsch.***
Varietal Denomination: USDA-ARS Summer Joy

(71) Applicant: The United States of America, as represented by the Secretary of Agriculture, Washington, DC (US)

(72) Inventors: Chunxian Chen, Warner Robins, GA (US); William R Okie, Augusta, GA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 19/444,429

(22) Filed: Jan. 9, 2026

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./180, 194, 197
See application file for complete search history.

*Primary Examiner* — Susan McCormick Ewoldt
(74) *Attorney, Agent, or Firm* — John Fado; Maria Restrepo-Hartwig

(57) ABSTRACT

A new and distinct cultivar of peach tree, denominated 'USDA-ARS Summer Joy', has firm, melting, clingstone fruit with attractive red blush and yellow ground color, yellow flesh, normal acidity, pleasant flavor and eating quality at maturity. The fruit typically ripen in early to mid-June in Byron, GA. The tree has self-fertile showy pink flowers and semi-spreading growth habit. This cultivar has a winter chilling requirement of approximately 850 chill hours, crops well most years, and is suited for high chill areas.

4 Drawing Sheets

Latin name of the genus and species of the plant claimed: 'USDA-ARS Summer Joy' is a new cultivar of peach (*Prunus persica* [L.] Batsch.).

Cultivar denomination: The new peach tree is denominated 'USDA-ARS Summer Joy'.

BACKGROUND OF THE NEW PLANT

The present invention relates to a new and distinct peach cultivar designated 'USDA-ARS Summer Joy', botanically known as *Prunus persica* (L.) Batsch, and tested as BY94P5911, which resulted from a series of open-pollinated (OP) seedlings of BY88P3378, BY85P1305, BY82P3766, and BY78P1804 peaches (all USDA Byron advanced selections), and 'Fantasia' nectarine (unpatented). This new peach tree is adapted to a Southeastern subtropical climate with high chill in winters. Its high chilling requirement (~850 chill hours) and desired early mid ripening season make it worthy of commercial production trials for the fresh fruit market. Clonal plants were asexually propagated from the original 'USDA-ARS Summer Joy' tree by grafting on 'Guardian' peach seedling rootstocks in Byron, GA. These asexually propagated plants, along with all characteristics of the tree and the fruit, remained true-to-type to the original 'USDA-ARS Summer Joy' tree. There are no known effects of the standard rootstock on the scion cultivar characteristics.

'USDA-ARS Summer Joy' produces firm, melting, clingstone, yellow-flesh fruit with normal acidity, rich flavor, attractive red blush and yellow ground (skin) color, which ripens in early to mid-June in Byron, GA. 'USDA-ARS Summer Joy' is a promising candidate for commercial success in the early mid harvest season in that it has a high chilling requirement and crops very well with attractive fruit.

Byron, GA and has a subtropical climate and locates in plant hardiness zone 8. There are about 67 rainy days per year. Average annual precipitation (rainfall) is 1182.9 millimeters (~46.6 inches) with great monthly and yearly variabilities and frequent thunderstorms in summers. Summers are long, hot and humid. The average July high temperature is about 33.2° Celsius (~91.8° Fahrenheit). Winters are short, mild and with rare snow. The average January low temperature is about 1.2° Celsius (~34.2° Fahrenheit). The hours with temperatures below 7.2° Celsius (~45.0° Fahrenheit) vary between 600 and 1200 hours per year.

SUMMARY OF THE INVENTION

The new and distinct cultivar 'USDA-ARS Summer Joy' peach tree blooms around mid-March, approximately with 'Elberta' (unpatented) peach trees in Byron, GA. The estimated chilling requirement, based on bloom time, is approximately 850 chill hours. The blooming period and the blooming date are dependent on climatic conditions. The flower anthers are yellow, and leaf glands are reniform, characteristic of many standard peach cultivars.

The first fruit of 'USDA-ARS Summer Joy' ripen generally in early to mid-June (the early mid season) in Byron, GA, approximately in the harvest season of 'Gala', 'Juneprince' and 'Summerprince' (all three of which are unpatented). 'USDA-ARS Summer Joy' fruit tend to have approximately 70% red skin. 'USDA-ARS Summer Joy' trees are productive and crop reliably.

The potential for commercial production of fresh 'USDA-ARS Summer Joy' fruit is high because it is a reliable higher-chill alternative (~850 chill hours) in the harvest season.

BRIEF DESCRIPTION OF THE PHOTOGRAPHS

The accompanying drawings are color photographs that are taken at different times in Byron, GA and as nearly true as it is reasonably possible to make in a color illustration of this type:

FIG. 1 is a color photograph that shows a close view of typical ripening fruit of the new cultivar 'USDA-ARS Summer Joy'.

FIG. 2 is a color photograph that shows attractive shapes, skin and flesh colors, and clingstone of specimens of five 'USDA-ARS Summer Joy' fruit arranged in three columns: stem and blossom end view (column 1: top and bottom), suture and back side view (2), and the fifth fruit cut into back-suture longitudinal halves with and without the clingstone (3). Each square on the board is one square centimeter.

Figure 1:
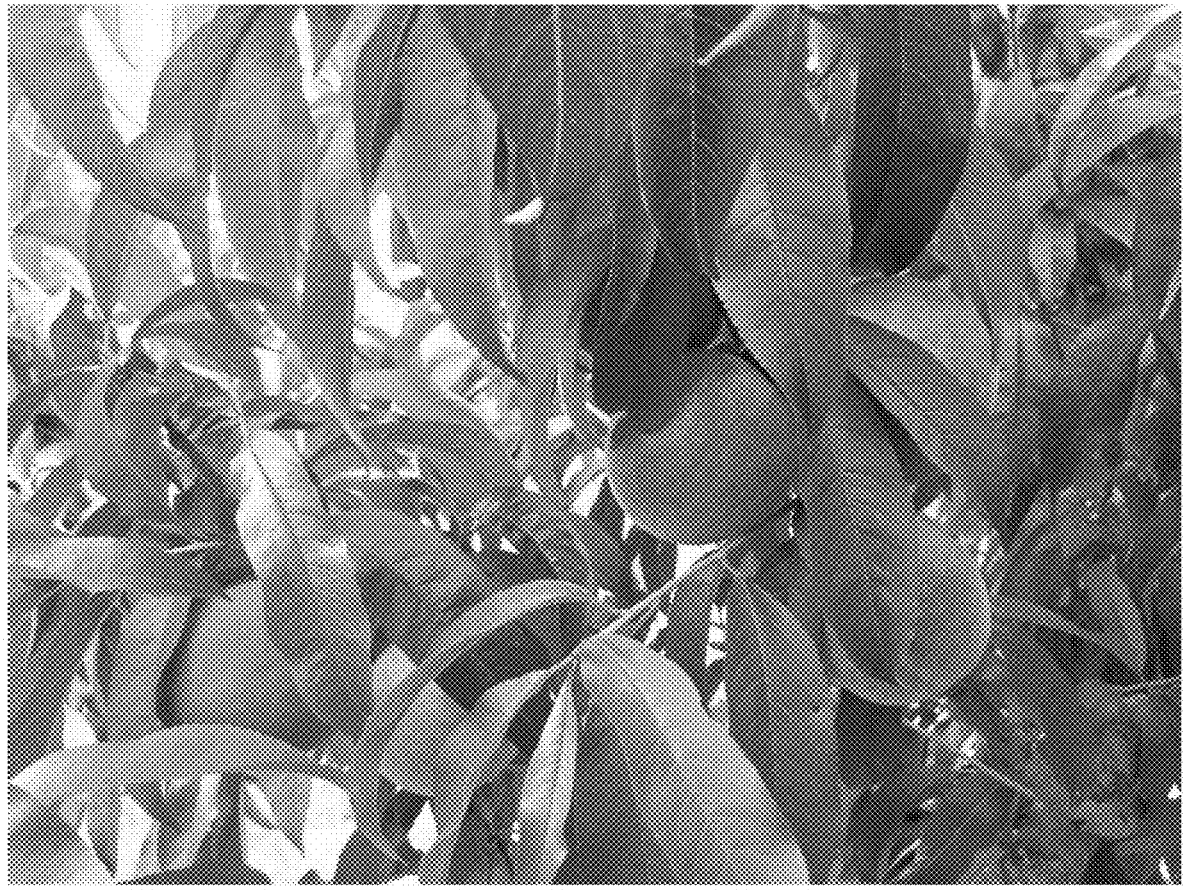
Figure 2:
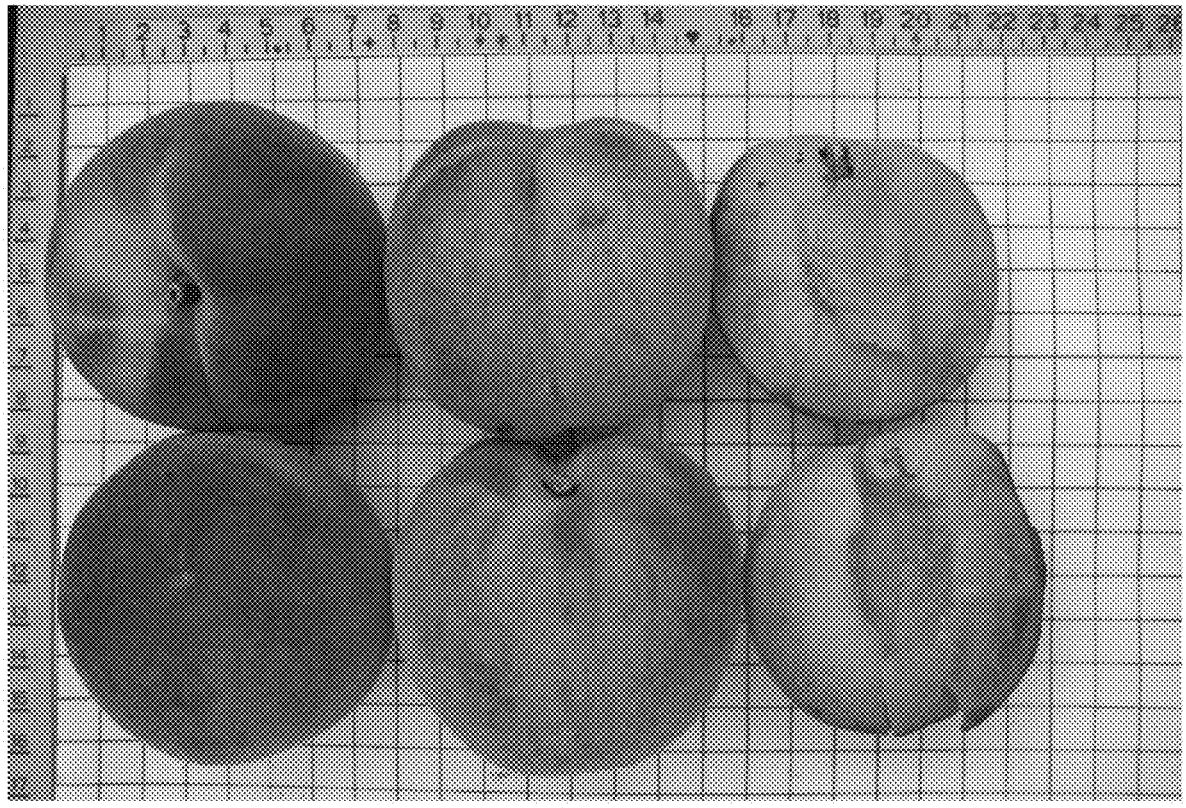
Figure 3:
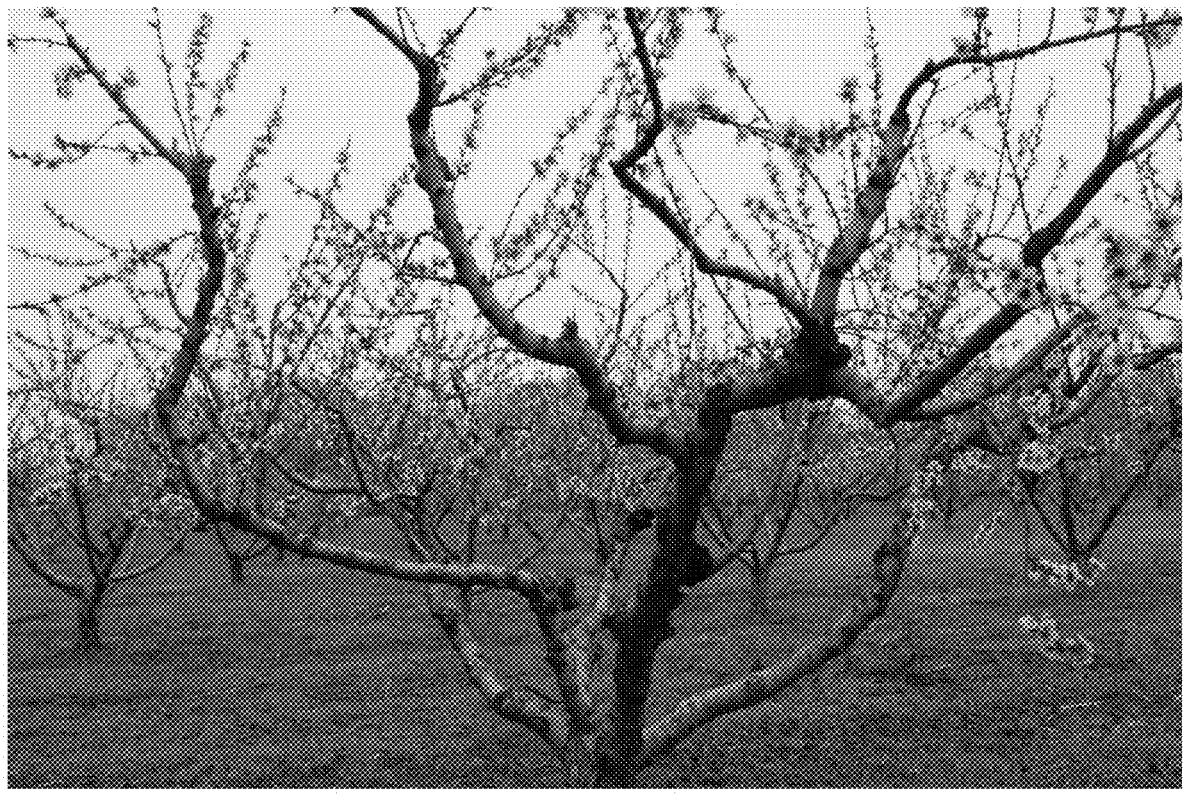
FIG. 3 is a color photograph that shows the typical semi-spreading architecture and showy flowers on a 12-year-old annually pruned tree of the new cultivar 'USDA-ARS Summer Joy'.
Figure 4:
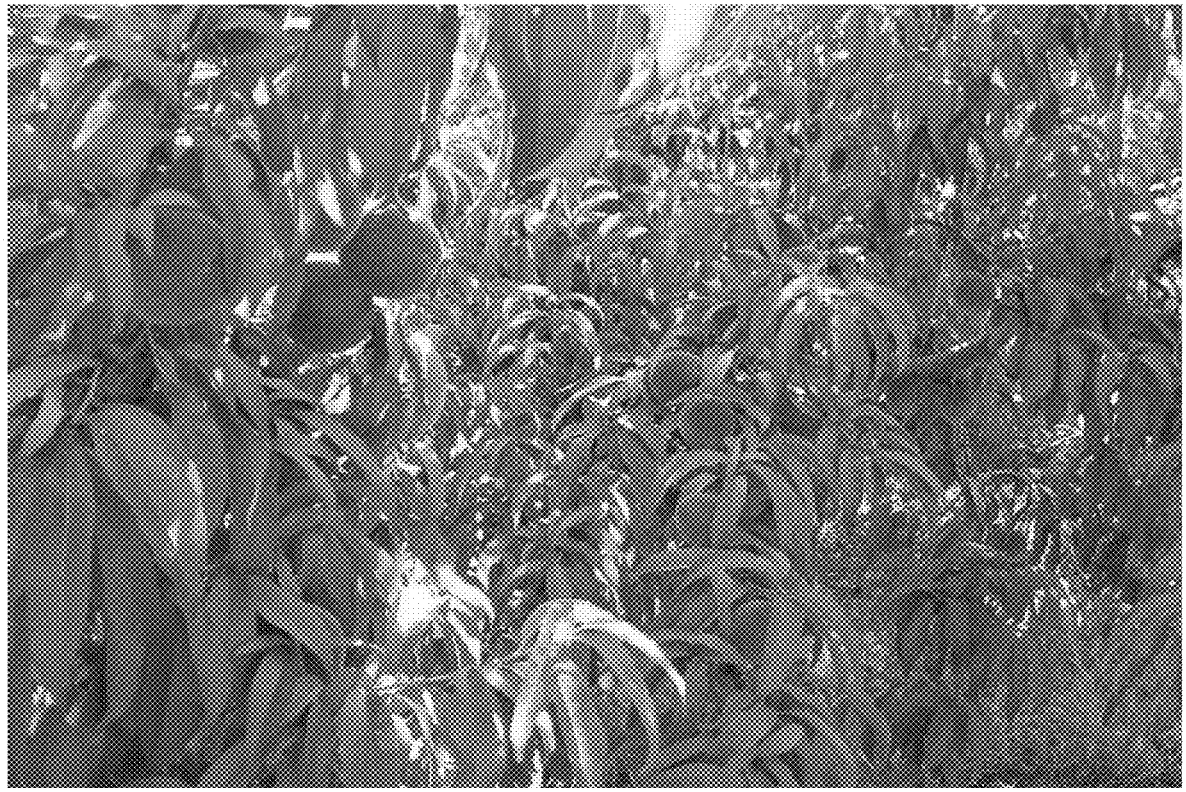
FIG. 4 is a color photograph that shows the distribution of attractive fruit ripening on a 12-year-old annually pruned tree of the new cultivar 'USDA-ARS Summer Joy'.

Due to digital camera equipment, image processing technologies, photographic parameters, production years, development stages, light, and other weather conditions, the leaves and fruit and their colors depicted in these photographs may or may not be authentic and consistent when compared to the actual botanical specimen.

DETAILED BOTANICAL DESCRIPTION

The tree, flowers, fruit, and other botanical parts may vary in slight detail due to variations in climatic conditions, cultural practices, development stages, growing seasons, soil types, and tree ages. Referring more specifically to the detailed botanical description of this new and distinct cultivar of yellow-flesh peach tree, the following was observed on 12-year-old trees of the cultivar grafted on 'Guardian' rootstock under the ecological conditions prevailing at the orchards located in Byron, GA, USA. All major color code designations are by reference to The Royal Horticultural Society (R.H.S.) Colour Chart (Fourth Edition).

Tree:

*Bearer*.—Regular. The fruit must be thinned to obtain large fruit size and avoid limb breakage.

*Canopy density*.—Considered dense. Pruning is required to open the tree center to promote sunlight entrance for enhancing fruit color and sugar.

*Estimated chilling requirement*.—Approximately 850 chill hours based on time of bloom and leafing in relation to standard cultivars.

*Vegetative bud break time*.—Mid to late March in Byron, GA, approximately 1 week after bloom depending on winter chill hours and amount of warm weather.

*Form*.—Semi-spreading but easily pruned to vase shape.

*Hardiness*.—Hardy with respect to typical GA winters.

*Productivity*.—Productive and regular in a typical capacity, based on fruit set ratings every year. Fruit set is reduced by thinning to develop the remaining fruit into desired market size. The fruit number or annual average production varies with the tree age, the prevailing climatic conditions, and cultural practices.

*Size*.—Generally considered large when trained to an open vase form. The height and width of 12-year-old annually pruned tree are 3.3 meters and 4.6 meters on average, respectively, including current season shoots.

*Spread*.—Grown to a vase shape with summer and winter pruning to keep the tree open to get strong fruiting wood in the lower center.

*Vigor*.—Considered moderately vigorous.

Trunk:

*Bark color*.—RHS Greyed-Green Group 196D. Bark crack's color is RHS Brown Group 200A.

*Size*.—On average approximately 19.2 centimeters in diameter at a height of approximately 30.0 centimeters on the 12-year-old trees at Byron, GA.

*Lenticel color*.—RHS Brown Group 201A outside and 200A inside.

*Lenticel count and size*.—On average approximately 3.3 per square centimeter of surface area of trunk; the average lenticel length and width of lenticels are approximately 9.5 millimeters and 3.2 millimeters, respectively.

Branches:

*Current season shoots*.—The color is RHS Greyed-Orange Group 176A at the upper part (sunny side) of the shoots and RHS Yellow-Green Group 145B at the lower part (shady side) of the shoots.

*Current fruiting limbs*.—The color is RHS Brown Group 200D at the upper part (sunny side) of the limbs and RHS Greyed-Orange Group 177D at the lower part (shady side) of the limbs.

*Crotch angles*.—Generally acute within the normal range of standard cultivars for a semi-spreading tree after proper summer and winter pruning.

*Internode length*.—Approximately 1.7 to 2.9 centimeters with the average of 2.4 centimeters.

*Surface texture*.—Relatively smooth. Roughness increases with age.

Leaves:

*Size*.—Considered medium to large for the species. The length is approximately 15.3 to 17.2 centimeters with the average of 16.0 centimeters, not including the petiole. The width is approximately 3.3 to 4.1 centimeters with the average of 3.9 centimeters. The thickness is regular and average for commercial cultivars, approximately 0.11 to 0.15 millimeters with the average of 0.14 millimeter, not noticeably unusual.

*Form*.—Lanceolate.

*Apex*.—Acute.

*Base*.—Acute.

*Margin*.—Serrulate.

*Surface*.—Upper, glabrous; Lower, medium to large veins that are pinnately netted.

*Color*.—Regular green, slightly different in seasons. In early season growth, both upper and lower leaf surfaces' color is RHS Yellow-Green Group 146B. In late season growth, upper leaf surface is RHS Green Group 137A and lower surface is RHS Yellow-Green Group 148B. Leaf vein is RHS Greyed-Yellow Group 160D.

*Glands*.—Reniform. Color is RHS Greyed-Orange Group 163A. Usually 0-3 on lower leaf blade and 2-4 on petioles. The length is approximately 1.2 to 1.9 millimeters with the average of 1.4 millimeters and width 0.5 to 0.9 millimeters with the average of 0.7 millimeters.

*Petiole*.—Color is RHS Green Group 138B. The length is approximately 7.3 to 12.8 millimeters with the average of 9.8 millimeters. The diameter is approximately 1.7 to 2.1 millimeters with the average of 1.9 millimeters.

*Stipules*.—Not Seen.

Flowers:

*Flower buds*.—The form, dimension, and size of flower buds vary greatly at different development stages and change rapidly as blooming approaches. They are conic at pre-floral dormant stage and approximately 5.5 to 7.8 millimeters long and 2.8 to 4.3 millimeters wide. The bud color in mid-winter is RHS Greyed-Purple Group 187A.

*Hardiness*.—Hardy with respect to GA winters.

*Date of bloom*.—Mid to late March depending on winter chilling and amount of warm weather.

*Blooming time*.—Considered medium-late in bloom relative to other commercial peaches in central GA. Typically blooms with 'Elberta'.

*Duration of bloom*.—Approximately 6 to 14 days. This characteristic varies significantly with amount of winter chilling as well as temperatures during bloom.

*Bloom quantity*.—Generally abundant, with a good distribution.

*Flower bud frequency*.—Generally one or two flower buds per node.

*Fragrance*.—Undetectable or faint floral scent.

*Type*.—Showy.

*Shape*.—Rosette.

*Fertility*.—Self-fertile.

*Flower size*.—Approximately 15.7 to 37.7 millimeters in diameter at full bloom, with the average of 26.5 millimeters.

*Petal*.—The color is RHS Purple Group 65A in the upper surface and RHS Purple Group 65B in the lower surface. The count is almost always five. The form is generally round shaped. The arrangement is usually free, sometimes touching. The texture is smooth, soft and glabrous. The margin is generally slightly undulating. The apex is generally round and curve shaped. The length is approximately 12.7 to 18.4 millimeters with the average of 15.3 millimeters. The width is approximately 8.5 to 15.5 millimeters with the average of 10.8 millimeters.

*Pedicel*.—The color is RHS Green Group 143B. The length is approximately 3.2 to 6.8 millimeters with the average of 4.6 millimeters. The diameter is approximately 1.5 to 3.3 millimeters with the average of 2.3 millimeters.

*Calyx cup*.—The color is RHS Orange Group 25A at the interior surface and Greyed-Purple Group 183B at the exterior surface. The diameter is approximately 7.0 to 11.0 millimeters with the average of 8.5 millimeters.

*Sepals*.—The color is RHS Greyed-Purple 183B. The number is generally five. The length is approximately 4.0 to 5.7 millimeters with the average of 5.1 millimeters. The width is approximately 4.2 to 6.3 millimeters with the average of 5.2 millimeters.

*Stamen number*.—Approximately 24 to 38 stamens per flower with the average of 31.8.

*Anthers*.—The color is RHS Yellow-Orange 22A at opening.

*Pollens*.—The color is RHS Yellow Group 9B and generally abundant.

*Filaments*.—The color is RHS Red-Purple Group 65D. The length at opening is approximately 2.9 to 8.2 millimeters with the average of 5.7 millimeters.

*Pistil*.—Usually one. The color is RHS Yellow-Green Group 145B (pistil tip color is RHS Green Group 143C). The length is approximately 5.3 to 13.4 millimeters with the average of 9.7 millimeters.

Fruit:

*Maturity when described*.—Tree ripe, Jun. 6, 2018 in Byron, GA, and firm in ripe conditions.

*Date of harvest*.—Varies with the prevailing climatic conditions. The picking starts first on Jun. 6, 2018 in Byron, GA.

*Size*.—Generally uniform medium to large size. The weight is approximately 153.5 to 186.1 grams with the average of 168.3 grams. The equatorial diameter is approximately 67.1 to 72.1 millimeters with the average of 68.6 millimeters. The polar diameter (from stem to distal end) in the suture-back circle is approximately 66.4 to 70.4 millimeters with the average of 68.1 millimeters; and that in the cheek-cheek circle is approximately 68.8 to 71.0 millimeters with the average of 68.4 millimeters. This characteristic highly depends on fruit number per tree, climate, soil type, cultural practices and environmental conditions, and therefore is not particularly distinctive of the cultivar.

*Peduncle*.—The color is RHS Green Group 138C. The length is approximately 4.1 to 5.8 millimeters with the average of 5.1 millimeters. The width is approximately 2.8 to 3.9 millimeters with the average of 3.5 millimeters.

*Longitudinal section form*.—Generally ovate.

*Transverse section through diameter*.—Usually round.

*Suture*.—Smooth or slightly indented from stem to tip.

*Ventral surface*.—Generally smooth.

*Shape of fruit base*.—Generally round.

*Apex*.—Generally ovate.

*Crater at stem attachment*.—The depth is approximately 5.5 to 14.7 millimeters with the average of 10.5 millimeters. The width at top is approximately 8.0 to 31.1 millimeters with the average of 19.5 millimeters at top.

*Skin*.—The blush and ground color is RHS Greyed-Purple 187A and Yellow 8B, respectively. The blush coverage is approximately 70% and may be higher with the ripening progress or in some production years. The thickness is approximately 0.1 to 0.3 millimeters with the average of 0.2 millimeters. The texture is generally typical of commercial peach cultivars. The tenacity to flesh is low and smooth. The tendency to crack is not observed. The taste is pleasant with no astringency observed. The epidermis is typical short pubescence.

*Flesh*.—Ripening evenly within each fruit. The color is RHS Yellow-Orange 17B. The color of red flecks within flesh is RHS Red 39A. The color of flesh at the stone is RHS Yellow-Orange 17B. The texture is smooth and firm when fully ripe. The fiber is very fine, small, tender, and abundant. The aroma is typical of commercial peach cultivars. The eating quality is typical, with pleasant flavor and acidity for fresh consumption. The soluble solid content is approximately 8.1 to 11.4° Brix with the average of 9.3° Brix. The titratable acidity is approximately 0.4 to 0.8% with the average of 0.6%. Browning by oxidation is not observed on tree ripe fruit beginning to soften. The juice is moderately abundant.

Stone:

*Type*.—Clingstone.

*Color*.—RHS Greyed-Orange 167D when freshly cut.

*Form*.—Oblong.

*Base*.—Obtuse.

*Apex*.—Acute.

*Sides*.—Equal.

*Surface*.—Generally furrowed.

*Tendency to split*.—None observed.

*Size*.—Varies upon the tree vigor, crop load and prevailing growing conditions. The length is approximately 28.4 to 36.0 millimeters with the average of 32.6 millimeters. The width is approximately 19.6 to 24.4 millimeters with the average of 22.2 millimeters. The cheek to cheek thickness is approximately 17.4 to 19.3 millimeters with the average of 18.2 millimeters.

*Wall thickness at cheek*.—Approximately 5.9 to 6.8 millimeters with the average of 6.3 millimeters.

*Kernel*.—Not viable if stratified upon removal from fruit at harvest. The color is RHS White 155D. The taste is bitter. The shape is generally ovate with acute tip and obtuse base. The length is approximately 15.6 to 17.6 millimeters with the average of 16.7 millimeters. The width is approximately 9.2 to 10.6 millimeters with the average of 9.8 millimeters. The cheek to cheek thickness is approximately 3.2 to 6.2 millimeters with the average of 5.3 millimeters.

Use of the fruit: Fresh, dessert.

Keeping quality: Considered average.

Shipping quality: Considered good. The fruit retained firmness and showed no internal breakdown of flesh or appreciable loss of eating quality under refrigeration at approximately 2 to 8 degrees Celsius indicates fruit should be highly acceptable for shipping.

Resistance to disease: Considered moderate or acceptable resistance to bacterial spot incited by *Xanthomonas campestris* pv. *pruni* in field trials. No other unusual resistance or susceptibility to insects and diseases was noted under standard management.

We claim:

1. A new and distinct cultivar of peach tree named 'USDA-ARS Summer Joy' as illustrated and described, characterized by fruit ripening in early to mid-June with attractive red blush and yellow ground color, clingstone, melting texture, yellow flesh, normal acidity, pleasant flavor and eating quality.

* * * * *